United States Patent
Oetter et al.

(10) Patent No.: US 6,451,753 B2
(45) Date of Patent: Sep. 17, 2002

(54) SOLID COMPOSITION CONSISTING OF HETEROCYCLIC COMPOUNDS AND/OR OXIME ESTERS AND INERT POROUS CARRIER MATERIALS AND THE USE THEREOF AS STABLE BLEACH ACTIVATOR COMPONENT IN DETERGENTS, BLEACHES AND CLEANERS

(75) Inventors: Günter Oetter, Frankenthal; Thomas Wehlage, Speyer; Elisabeth Kappes, Limburgerhof; Reinhard Müller, Friedelsheim; Dieter Boeckh, Limburgerhof; Michael Schönherr, Frankenthal, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/091,238
(22) PCT Filed: Mar. 6, 1997
(86) PCT No.: PCT/EP97/01125
§ 371 (c)(1), (2), (4) Date: Jun. 16, 1998
(87) PCT Pub. No.: WO97/33964
PCT Pub. Date: Sep. 18, 1997

(30) Foreign Application Priority Data

Mar. 14, 1996 (DE) .......................... 196 09 953

(51) Int. Cl.⁷ .............................. C11D 3/28; C11D 3/32
(52) U.S. Cl. ........................................ 510/376; 510/377
(58) Field of Search ................................. 510/376, 377

(56) References Cited

U.S. PATENT DOCUMENTS

| | | | |
|---|---|---|---|
| 5,534,195 A | * | 7/1996 | Chapman et al. ............ 510/444 |
| 5,534,196 A | * | 7/1996 | Chapman et al. ...... 252/186.27 |

FOREIGN PATENT DOCUMENTS

| | | |
|---|---|---|
| DE | 30 03 351 A | 8/1981 |
| DE | A 30 03 351 | 8/1981 |
| DE | 34 44960 A | 6/1986 |
| DE | A 195 18 039 | 11/1996 |
| DE | 195 18 039 A | 11/1996 |
| EP | 0 122 763 A | 10/1984 |
| EP | A 0 122 763 | 10/1984 |
| EP | 0 170 386 A | 2/1986 |
| EP | A 0 267 046 | 5/1988 |
| EP | 0 267 046 A | 5/1988 |
| EP | 0 382 464 A | 8/1990 |
| FR | A 2 398 798 | 2/1979 |
| FR | 2 398 798 A | 2/1979 |
| GB | A 2 249 104 | 4/1992 |
| GB | 2 249 104 A | 4/1992 |
| JP | 6 336 468 A | 12/1994 |
| WO | WO 93 04037 | 3/1993 |
| WO | WO 94/28102 | * 12/1994 |
| WO | WO94/28106 | * 12/1994 |
| WO | WO 95/07883 | * 3/1995 |
| WO | WO 95/28464 | * 10/1995 |

OTHER PUBLICATIONS

"Reagents for Organic Synthesis", L.F. Fieser et al., John Wiley & Sons, Inc., Nov. 1967, pp. 703–704.*
Jumar, et al., Z. Chem., 7 Jg.(1967)Heft 9, pp. 344–345.

* cited by examiner

Primary Examiner—John Hardee
(74) Attorney, Agent, or Firm—Oblon, Spivak, McClelland, Maier & Neustadt, P.C.

(57) ABSTRACT

A solid composition consisting essentially of 5–98 parts by weight of heterocyclic compounds I

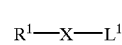

$$R^1\text{—}X\text{—}L^1 \qquad (I)$$

where
  $L^1$ is groups with a cyclic carbamate, a lactonoxy or a lactam structure,
  X is a carbonyl, a doubled carbonyl or a heterocarbonyl group, and
  $R^1$ is an organic radical or a second moiety $L^1$,
and/or oxime esters II

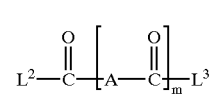

$$L^2\text{—}\overset{\overset{O}{\|}}{C}\text{—}[A\text{—}\overset{\overset{O}{\|}}{C}]_m\text{—}L^3 \qquad (II)$$

where
  $L^2$ is an oxime moiety

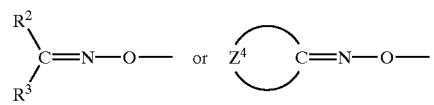

where
  $R^2$, $R^3$ and $Z^4$ are organic radicals or linkers,
  $L^3$ is the radical $R^1$, a second oxime moiety $L^2$ or a carboxylic ester residue, carboxamide residue, phenolate residue, vinyloxy radical, sulfonamide residue, imidazole residue, amidolactam residue, cyclic carbamate residue, lactonoxy residue or lactam residue, and
  m is 0 or 1,
and 2–95 parts by weight of inert porous carrier materials with an internal surface area of from 10 to 500 m²/g.

The solid composition described is suitable as stable bleach activator component in detergents, bleaches and cleaners.

17 Claims, No Drawings

SOLID COMPOSITION CONSISTING OF HETEROCYCLIC COMPOUNDS AND/OR OXIME ESTERS AND INERT POROUS CARRIER MATERIALS AND THE USE THEREOF AS STABLE BLEACH ACTIVATOR COMPONENT IN DETERGENTS, BLEACHES AND CLEANERS

The present invention relates to a solid composition consisting of heterocyclic compounds with cyclic carbamate, lactonoxy or lactam structure and/or oxime esters and inert porous carrier materials whose internal surface area has a particular value. The invention furthermore relates to a process for preparing this solid composition and to its use in detergents, bleaches and cleaners, especially as stable bleach activator component.

A number of cold bleach activators, including some of the compounds I and II defined hereinafter, are liquid or plastic in the pure form and, accordingly, can be converted only with great difficulty into free-flowing granules or powders using conventional auxiliaries and formulation methods. Free-flowing formulations with no tendency to agglomerate are, however, required for use in detergent and some cleaner formulations.

Conventional drying processes for producing solids from solutions, such as spray drying, frequently give unsatisfactory results for cold bleach activators which are solid in pure form, because these substances are, as a rule, very hygroscopic and mostly have relatively low melting points. The applicability of crystallization processes is just as low because these substances are often prone to form supersaturated solutions, i.e. crystallization is greatly inhibited and thus uncontrollable.

It is an object of the present invention to provide a storage-stable solid, free-flowing form for cold bleach activators with a heterocyclic structure, in particular using auxiliaries which are described in large numbers in the prior art for such purposes. It was moreover intended that these compositions also be improved in their formulated form with regard to the dissolving rate and the activity in the wash liquor.

Thus, for example, DE-A 27 33 849 (1) discloses solid cold bleach activator formulations for detergents and cleaners, the only cold bleach activators mentioned are acyl compounds such as diacetyl-methylamine or diacetylbutylamine. These cold bleach activators are mixed with adsorbents such as kieselguhr, silicates, silicas or aluminum oxide. However, (1) contains no information on the internal surface area and average particle size of these adsorbents.

DE-A 34 44 960 (2) relates to a coarse-particle adsorbent for liquid and pasty detergent and cleaner formulations which may, inter alia, contain bleach activators. The granules of adsorbent and detergent or cleaner formulation produced in this way can also be dusted or surface-coated with fine-particle powders. Examples of such dusting powders are zeolites or silica aerogel with a particle size of from 0.001 to 0.1 mm, but no information is given on their internal surface area.

EP-A 170 386 (3) discloses bleach systems which contain as bleaching agent inter alia N-acyl- or N-benzoyl-6-aminoperoxy-caproic acid. These bleach systems are employed in detergent formulations which contain sodium aluminum silicates, eg. zeolite A, as builder which is present separate from the bleach system.

EP-A 382 464 (4) discloses a coating or encapsulation process for solid particles or liquid drops, for example bleaches, with polyethylene glycols, polyethylene oxides, polyvinylpyrrolidone, oxidized polyethylene or similar substances. In this case, fine-particle substances such as Aerosil® 380 or Aerosil R 972 are added as formulation aids ("crumbling agents").

We have now found a solid composition consisting essentially of 5–98 parts by weight of heterocyclic compounds of the general formula I $$R^1\text{—}X\text{—}L^1 \tag{I}$$

where $L^1$ is (a) a cyclic carbamate residue of the formula

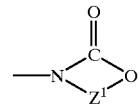

(b) a lactonoxy residue of the formula

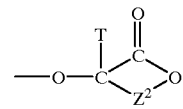

or (c) a lactam residue of the formula

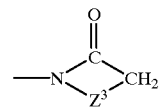

where $Z^1$ to $Z^3$ are 1,2-, 1,3-, 1,4- or 1,5-alkylene groups which have 2 to 20 carbon atoms, and which can additionally be functionalized by one to three hydroxyl groups, $C_1$-$C_4$-alkoxy groups, amino groups, $C_1$-$C_4$-alkylamino groups, di-$C_1$-$C_4$-alkylamino groups, chlorine atoms, bromine atoms, nitro groups, cyano groups, carboxyl groups, sulfo groups, carboxy-$C_1$-$C_4$-alkyl groups, carboxamide groups or phenyl, tolyl or benzyl radicals, it likewise being possible for aromatic nuclei in turn to be substituted by said radicals, or interrupted by one or two non-adjacent oxygen atoms, amino groups, $C_1$-$C_4$-alkylamino groups or carbonyl groups, and T is hydrogen or $C_1$-$C_4$-alkyl, X is an oxygen-containing group of the formula

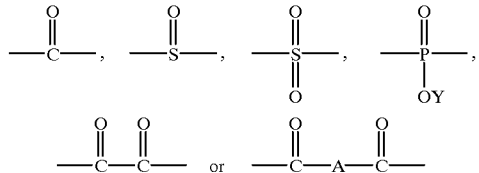

where

Y is hydrogen, ammonium which can be unsubstituted or substituted by organic radicals, or $C_1$-$C_4$-alkyl, and A is a chemical bond or a $C_1$-$C_{18}$-alkylene group, a $C_2$-$C_{18}$-alkenylene group, a $C_5$-$C_{32}$-cycloalkylene group, a $C_7$-$C_{30}$-aralkylene group, a $C_6$-$C_{18}$-arylene group or a $C_3$-$C_{18}$-hetarylene group, it additionally being possible for aliphatic structural units to be functionalized by one to five hydroxyl groups, $C_1$-$C_4$-alkoxy groups, amino groups, $C_1$-$C_4$-alkylamino groups, di-$C_1$-$C_4$-alkylamino groups, chlorine atoms, bromine atoms, nitro groups, cyano groups, carboxyl groups, sulfo groups, carboxy-$C_1$-$C_4$-alkyl groups, carboxamide groups or phenyl, tolyl or benzyl radicals, it likewise being possible for aromatic, cycloaliphatic and hetero-aromatic structural units to be substituted by said radicals, or interrupted by one to eight non-adjacent oxygen atoms, amino groups, $C_1$-$C_4$-alkylamino groups or carbonyl groups, and $R^1$ has the following meaning: $C_1$-$C_{30}$-alkyl, $C_2$-$C_{30}$-alkenyl, $C_5$-$C_{18}$-cycloalkyl, $C_7$-$C_{18}$-aralkyl, $C_6$-$C_{18}$-aryl or $C_3$-$C_{18}$-hetaryl, it being additionally possible for aliphatic radicals to be functionalized by one to five hydroxyl groups, $C_1$-$C_4$-alkoxy groups, amino groups, $C_1$-$C_4$-alkylamino groups, di-$C_1$-$C_4$-alkylamino groups, chlorine atoms, bromine atoms, nitro groups, cyano groups, carboxyl groups, sulfo groups, carboxy-$C_1$-$C_4$-alkyl groups, carboxamide groups or phenyl, tolyl or benzyl radicals, it likewise being possible for aromatic, cycloaliphatic and heteroaromatic structural units to be substituted by said radicals, or interrupted by one to eight non-adjacent oxygen atoms, amino groups, $C_1$-$C_4$-alkylamino groups or carbonyl groups, or a heterocyclic radical $L^1$, and/or oxime esters of the general formula II

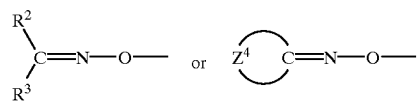

(II)

where $L^2$ is an oxime moiety of the formula

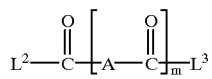  or  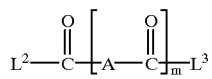

where $R^2$ and $R^3$ are hydrogen, $C_1$-$C_{30}$-alkyl, $C_2$-$C_{30}$-alkenyl, $C_5$-$C_{18}$-cycloalkyl, $C_7$-$C_{18}$-aralkyl, $C_6$-$C_{18}$-aryl or $C_3$-$C_{18}$-hetaryl, it being additionally possible for aliphatic radicals to be functionalized by one to five hydroxyl groups, $C_1$-$C_4$-alkoxy groups, amino groups, $C_1$-$C_4$-alkylamino groups, di-$C_1$-$C_4$-alkylamino groups, chlorine atoms, bromine atoms, nitro groups, cyano groups, carboxyl groups, sulfo groups, carboxy-$C_1$-$C_4$-alkyl groups, carboxamide groups or phenyl, tolyl or benzyl radicals, it likewise being possible for aromatic, cycloaliphatic and heteroaromatic structural units to be substituted by said radicals, or interrupted by one to eight non-adjacent oxygen atoms, amino groups, $C_1$-$C_4$-alkylamino groups or carbonyl groups, and $Z^4$ is 1,3-, 1,4-, 1,5-, 1,6-, 1,7- or 1,8-alkylene groups which have 3 to 30 carbon atoms and which can additionally be functionalized by one to five hydroxyl groups, $C_1$-$C_4$-alkylamino groups, di-$C_1$-$C_4$-alkylamino groups, chlorine atoms, bromine atoms, nitro groups, cyano groups, carboxyl groups, sulfo groups, carboxy-$C_1$-$C_4$-alkyl groups, carboxamide groups or phenyl, tolyl or benzyl radicals, it likewise being possible for aromatic nuclei in turn to be substituted by said radicals, or interrupted by one or two non-adjacent oxygen atoms, amino groups, $C_1$-$C_4$-alkylamino groups or carbonyl groups, $L^3$ is the radical $R^1$, a second oxime moiety $L^2$ or (a) a carboxylic ester residue of the formula

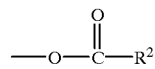

(b) a carboxamide residue of the formula

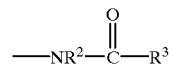

(c) a phenolate residue of the formula

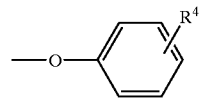

(d) a vinyloxy radical of the formula

(e) a sulfonamide residue of the formula

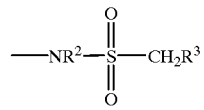

(f) an imidazole residue of the formula

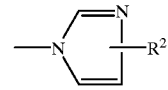

(g) an amidolactam residue of the formula

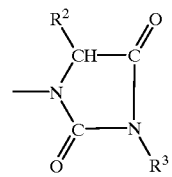

(h) a cyclic carbamate residue of the formula

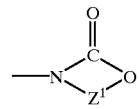

(j) a lactonoxy residue of the formula

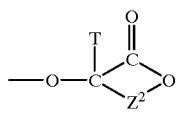

or (k) a lactam residue of the formula

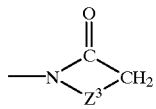

where
$R^1$, $R^2$, $R^3$, T, $Z^1$ to $Z^3$ and A have the abovementioned meanings, $R^4$ is hydrogen, a carboxyl group, a sulfo group, a phosphono group or the alkali metal or ammonium salt thereof, and m is the number 0 or 1 and 2–95 parts by weight of inert porous carrier materials with an internal surface area of from 10 to 500 m$^2$/g.

The variables $Z^1$ bis $Z^3$ in the heterocyclic systems (a) to (c) can be, in particular, $C_2$-$C_{10}$-alkylene groups of the following structure:

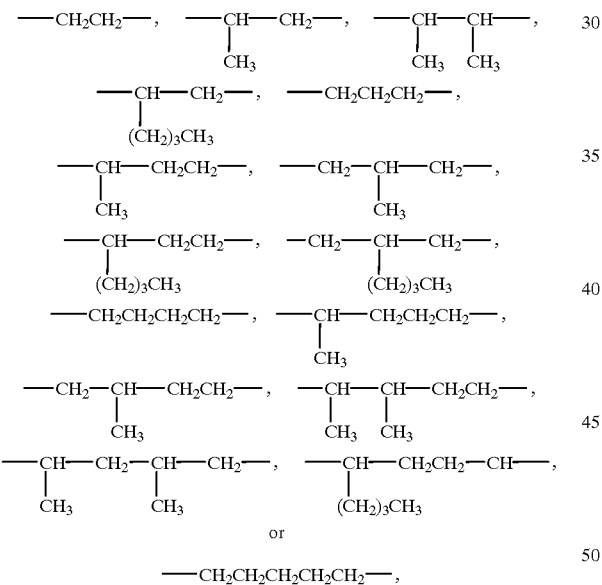

where, in the case of non-symmetrical alkylene groups, in principle both ways of incorporation into the rings are possible. The variables $Z^1$ to $Z^3$ can be functionalized or interrupted as stated.

Typical examples of the linker A are the following:

as linear or branched $C_1$-$C_{18}$-alkylene group, in particular $C_6$-$C_{12}$-alkylene group, it is possible for methylene, 1,2-ethylene, 1,1-ethylene, 1,3-propylene, 1,2-propylene, 1,1-propylene, 2,2-propylene, 1,4-butylene, 1,2-butylene, 2,3-butylene, pentamethylene, 3-methyl-1,5-pentylene, hexamethylene, heptamethylene, octamethylene, nonamethylene, decamethylene, undecamethylene, dodecamethylene, tetradecamethylene, hexadecamethylene or octadecamethylene to occur;

as linear or branched $C_2$-$C_{18}$-alkenylene group, in particular $C_6$-$C_{12}$-alkenylene group, it is possible for linkers with one, two or three olefinic double bonds to occur, eg. 1,2-ethenylene, 1,3-propenylene, 1,4-but-2-enylene, 1,6-hex-3-enylene, 1,8-oct-4-enylene or 1,12-dodec-6-enylene;

suitable as $C_5$-$C_{32}$-cycloalkylene groups, in particular $C_5$-$C_{10}$-cycloalkylene groups, are 1,2- or 1,3-cyclopentylene, 1,2-, 1,3- or 1,4-cyclohexylene, 1,2-, 1,3- or 1,4-cyclo-heptylene, 1,2-, 1,3-, 1,4- or 1,5-cyclooctylene or groups of the formula

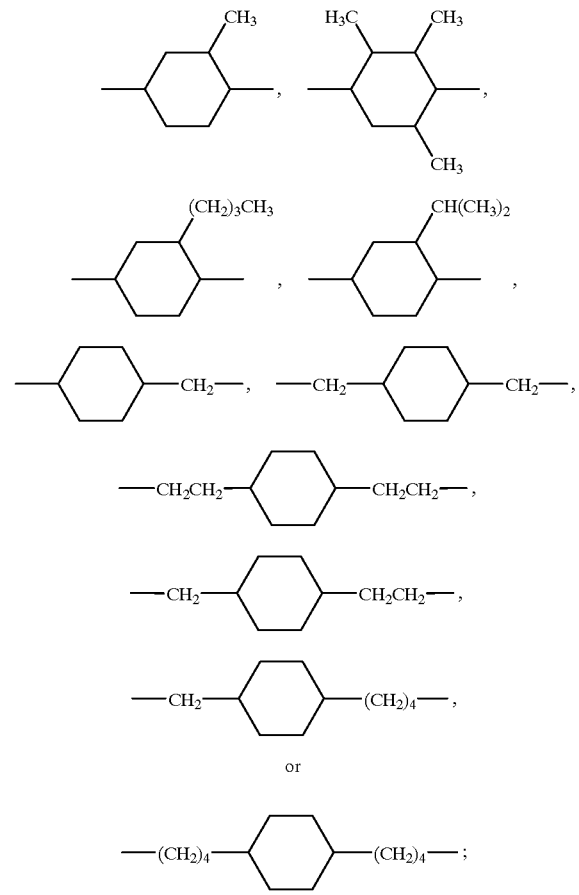

suitable as $C_7$-$C_{30}$-aralkylene groups, in particular unsubstituted or alkyl-substituted $C_7$-$C_{22}$-phenylalkylene and -diphenyl-alkylene groups, are groups of the formula

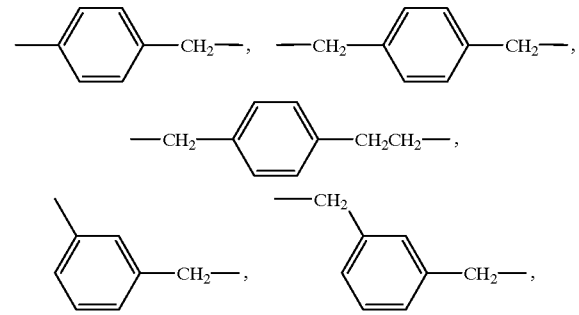

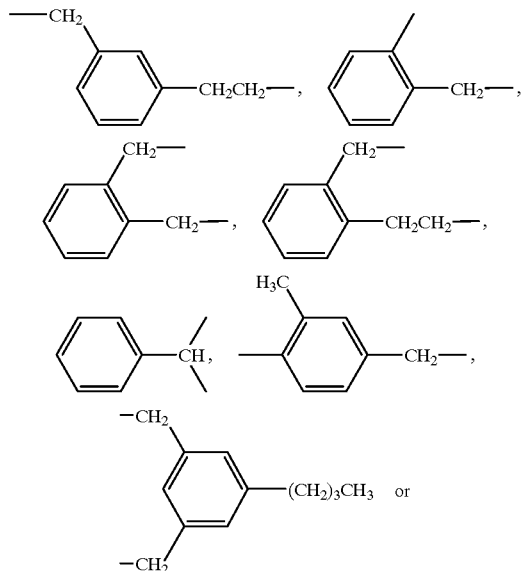

particularly suitable as $C_6$-$C_{18}$-arylene groups, in particular unsubstituted or alkyl-substituted phenylene, biphenylylene or naphthylene groups, are 1,4-, 1,3- and 1,2-phenylene, but also groups of the formula

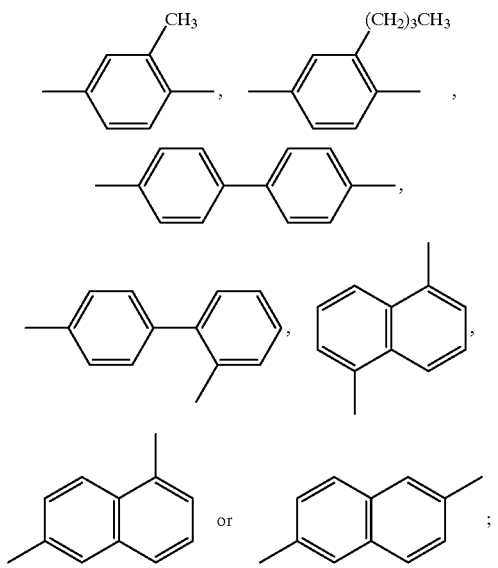

suitable as $C_3$-$C_{18}$-hetarylene groups, in particular five- or six-membered $C_3$-$C_{12}$-hetarylene groups with one or two hetero-atoms from the group of nitrogen, oxygen and sulfur, are groups of the formula

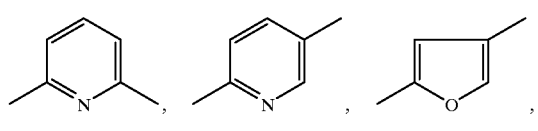

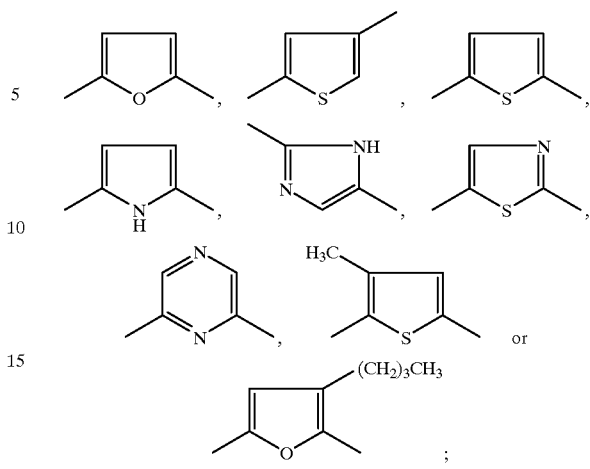

examples of suitable structures interrupted by oxygen or amino groups, in particular NH or $N(CH_3)$ groups, are the following structures:

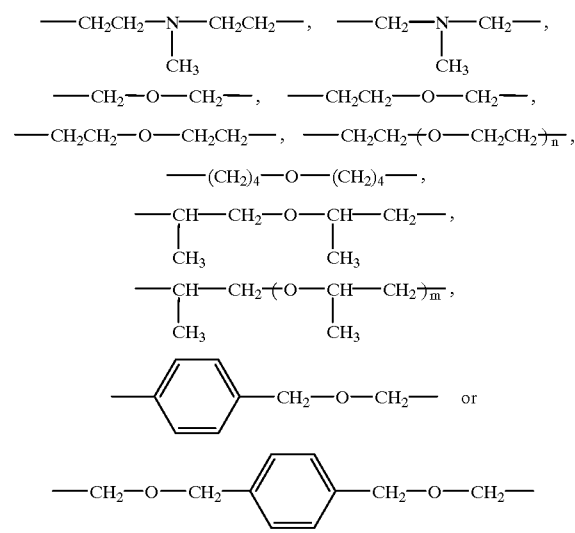

with n=2 to 8 and m=2 to 5.

Suitable meanings for the radical $R^1$ are the following:

suitable as $C_1$-$C_{30}$-alkyl group are, for example, methyl, ethyl, n-propyl, iso-propyl, n-butyl, iso-butyl, sec-butyl, tert-butyl, n-pentyl, iso-pentyl, sec-pentyl, tert-pentyl, neo-pentyl, n-hexyl, n-heptyl, n-octyl, 2-ethylhexyl, n-nonyl, iso-nonyl, n-decyl, n-undecyl, n-dodecyl, n-tridecyl, iso-tridecyl, n-tetradecyl, n-pentadecyl, n-hexadecyl, n-heptadecyl, n-octadecyl, n-nonadecyl or n-eicosyl; $C_6$-$C_{18}$-alkyl groups are preferred, especially $C_8$-$C_{12}$-alkyl groups;

suitable as $C_2$-$C_{30}$-alkenyl group are, for example, vinyl, allyl, 2-methyl-2-propenyl or the corresponding radical derived from oleic acid, linoleic acid or linolenic acid; $C_{16}$-$C_{22}$-alkenyl groups are preferred;

particularly suitable as $C_5$-$C_{18}$-cycloalkyl group are $C_5$-$C_{10}$-cycloalkyl groups, eg. cyclopentyl, cyclohexyl, 2-, 3- or 4-methylcyclohexyl, 2,3-, 2,4-, 2,5- or 2,6-dimethylcyclohexyl, cycloheptyl or cyclooctyl;

particularly suitable as $C_7$-$C_{18}$-aralkyl, in particular $C_7$-$C_{12}$-aralkyl, group are alkyl-substituted phenylalkyl groups, eg. benzyl, 2-, 3- or 4-methylbenzyl, 2-phenylethyl, 3-phenyl-propyl, 4-phenylbutyl, 2-, 3- or 4-ethylbenzyl, 3- or 4-isopropylbenzyl or 3- or 4-butylbenzyl;

suitable as $C_6$-$C_{18}$-aryl group are, for example, phenyl, 2-, 3-or 4-biphenylyl, α- or β-naphthyl, 2-, 3- or 4-methylphenyl, 2-, 3- or 4-ethylphenyl, 3- or 4-isopropylphenyl, 3- or 4-butylphenyl or 3- or 4-(2-ethylhexyl)phenyl; $C_6$-$C_{14}$-aryl groups are preferred, especially phenyl and alkyl-substituted phenyl;

particularly suitable as $C_3$-$C_{18}$-hetaryl group are five- or six-membered $C_3$-$C_{12}$-hetaryl groups with one or two heteroatoms from the group of nitrogen, oxygen and sulphur; examples thereof are:

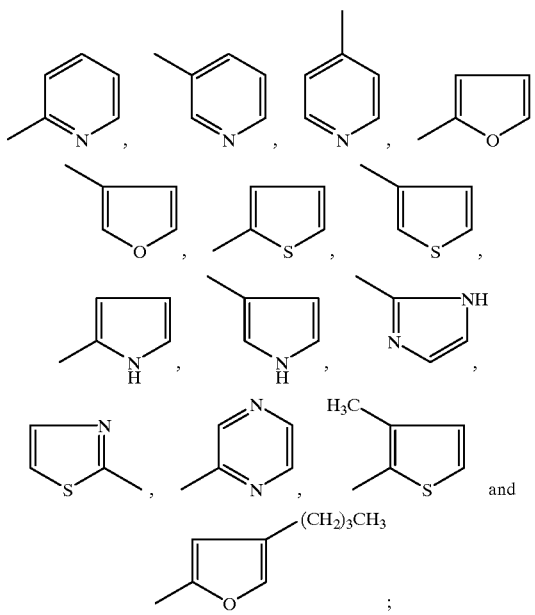

examples of suitable aliphatic radicals interrupted by oxygen or amino groups, in particular NH or N(CH$_3$) groups, are the following structures:

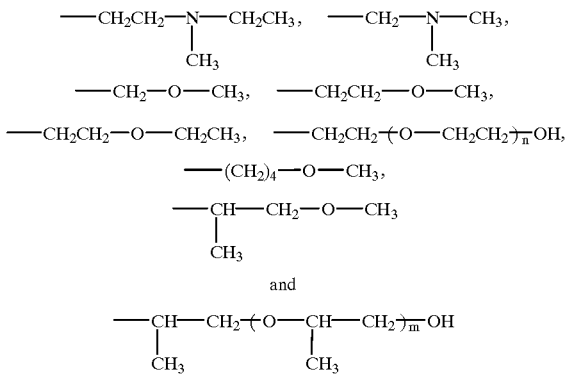

with n=2 to 8 and m=2 to 5.

The variables $Z^1$ to $Z^3$, A and $R^1$ defined above can additionally be functionalized by the stated groups. In this connection $C_1$-$C_4$-alkoxy groups are in particular methoxy, ethoxy, n-propoxy, isopropoxy, n-butoxy, isobutoxy, sec-butoxy or tert-butoxy. Preferred amino groups are —NH$_2$, —NH (CH$_3$), —NH (CH$_2$CH$_3$), —N(CH$_3$)$_2$ and —N(CH$_2$CH$_3$)$_2$. Examples of carboxy-$C_1$-$C_4$-alkyl groups are carboxymethyl, carboxyethyl, carboxypropyl, carboxybutyl or carboxy-tert-butyl.

The oxygen-containing group X in which one or two oxygen atoms are linked by a double bond on carbon, sulfur or phosphorus atoms, ie. are carbonyl or heterocarbonyl functionalities, is preferably

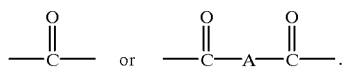

In the case where $R^1$=$L^1$, the two heterocyclic radicals $L^1$ bonded to the group X are preferably the same.

A particularly preferred solid composition is one in which the radical $R^1$ in the heterocyclic compounds I is $C_6$-$C_{18}$-alkyl, $C_6$-$C_{18}$-alkenyl, $C_7$-$C_{12}$-aralkyl, phenyl or alkyl-substituted phenyl with a total of up to 14 carbon atoms or a second heterocyclic radical $L^1$ which has the same structure as the first heterocyclic radical $L^1$. With a view to the preferred use of the heterocyclic compounds I as cold bleach activators in detergents, bleaches and cleaners, it has proven beneficial for $R^1$ to be a long-chain or bulky radical with corresponding hydrophobicity.

The following types of structures of the heterocyclic compounds I are preferably employed:

(1) N-Acyloxazolidones of the formula

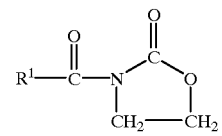

(2) N-Acyl-1,3-tetrahydrooxazinones of the formula

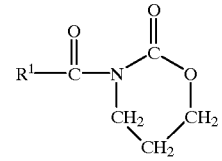

(3) Acyloxy-γ-butyrolactone der Formel

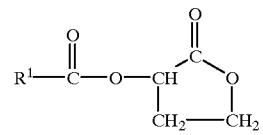

(4) Acyloxy-γ-valerolactones of the formula

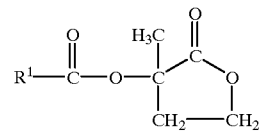

(5) O-Acylpantolactones of the formula

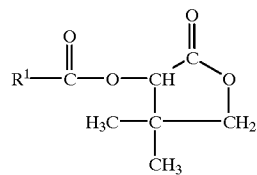

(6) Acyloxy-δ-valerolactones of the formula

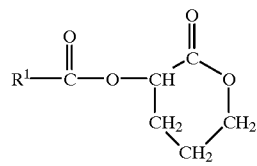

(7) Acyloxy-ε-caprolactones of the formula

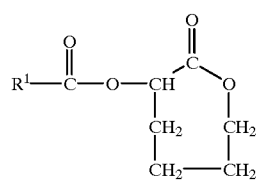

(8) Acyl-γ-butyrolactams of the formula

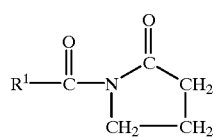

(9) N-Acyl-δ-valerolactams of the formula

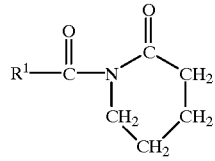

(10) N-Acyl-ε-caprolactams of the formula

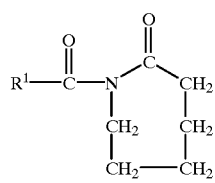

(11) N,N'-Carbonylbisoxazolidones of the formula

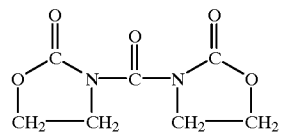

(12) N,N'-Carbonylbis-1,3-tetrahydrooxazinones of the formula

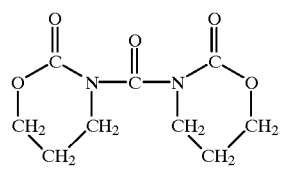

(13) Carbonic acid bis-γ-butyrolactones of the formula

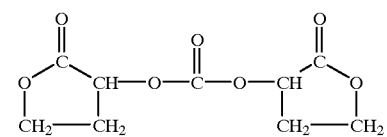

(14) Carbonic acid bis-γ-valerolactones of the formula

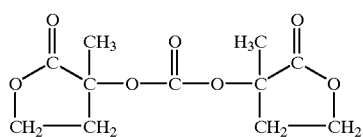

(15) O,O'-Carbonylbispantolactones of the formula

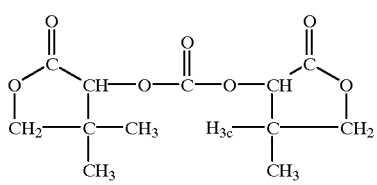

(16) Carbonic acid bis-δ-valerolactones of the formula

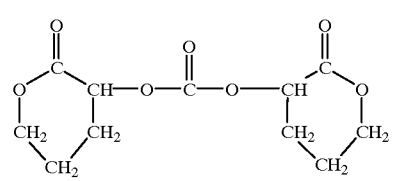

(17) Carbonic acid bis-ε-caprolactones of the formula

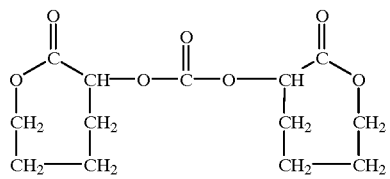

(18) N,N'-Carbonylbis-γ-butyrolactams of the formula

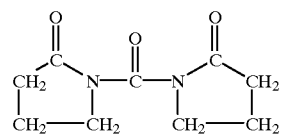

(19) N,N'-Carbonylbis-δ-valerolactams of the formula

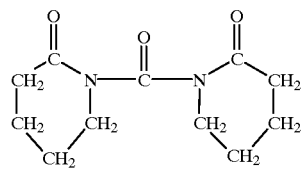

(20) N,N'-Carbonylbis-ε-caprolactams of the formula

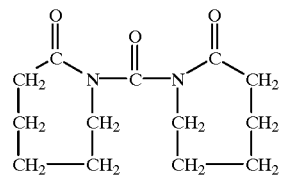

(21) doubled N-acyloxazolidones of the formula

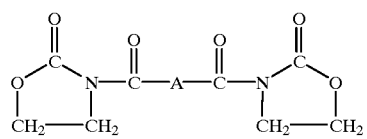

(22) doubled N-acyl-1,3-tetrahydrooxazinones of the formula

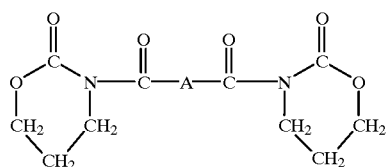

(23) doubled acyloxy-γ-butyrolactones of the formula

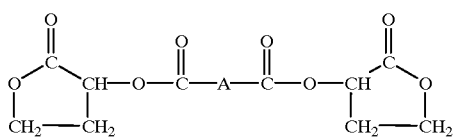

(24) doubled acyloxy-γ-valerolactones of the formula

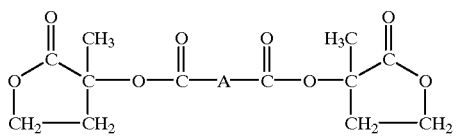

(25) doubled O-acylpantolactones of the formula

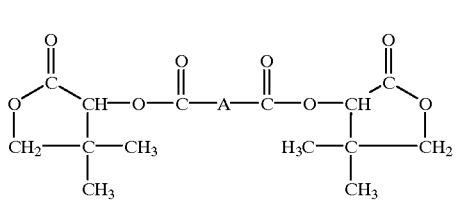

(26) doubled acyloxy-δ-valerolactones of the formula

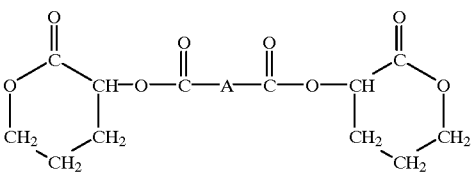

(27) doubled acyloxy-ε-caprolactones of the formula

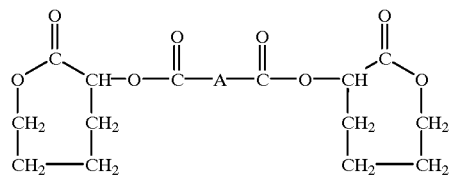

(28) doubled acyl-γ-butyrolactams of the formula

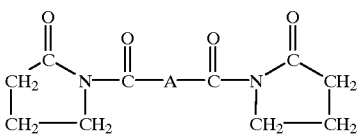

(29) doubled acyl-δ-valerolactams of the formula

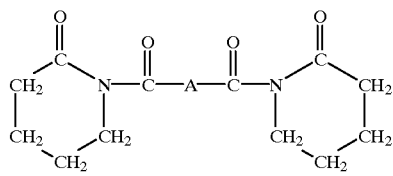

(30) doubled N-acyl-ε-caprolactams of the formula

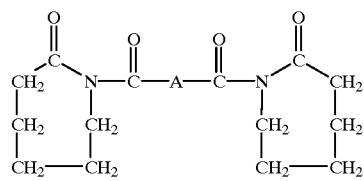

The radical $R^1$ in types (1) to (10) of structure is, in particular, n-hexyl, n-heptyl, n-octyl, n-nonyl, n-decyl, n-undecyl, n-dodecyl, cyclohexyl, benzyl, phenyl or 2-, 3- or 4-methyl-phenyl.

The linker A in types (21) to (30) of structure is, in particular, hexamethylene, octamethylene, decamethylene, dodeca-methylene, 1,3- or 1,4-cyclohexylene or 1,4-, 1,3- or 1,2-phenylene; of particular interest for A is 1,4-phenylene (derived from terephthalic acid).

The following meanings, besides hydrogen, are suitable for the radicals $R^2$ and $R^3$ in the oxime esters II, which can be identical or different:

- examples of suitable linear or branched $C_1$-$C_{30}$-alkyl groups are methyl, ethyl, n-propyl, iso-propyl, n-butyl, iso-butyl, sec-butyl, tert-butyl, n-pentyl, iso-pentyl, sec-pentyl, tert-pentyl, neo-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl; $C_1$-$C_{12}$-alkyl groups are preferred, especially $C_1$-$C_4$-alkyl groups;
- examples of suitable linear or branched $C_2$-$C_{30}$-alkenyl groups are vinyl, allyl, 2-methyl-2-propenyl or the corresponding radical derived from oleic acid, linoleic acid or linolenic acid; $C_2$-$C_6$-alkenyl and $C_{16}$-$C_{22}$-alkenyl groups are preferred;
- particularly suitable $C_5$-$C_{18}$-cycloalkyl groups are $C_5$-$C_{10}$-cycloalkyl groups, eg. cyclopentyl, cyclohexyl, 2-, 3- or 4-methylcyclohexyl, 2,3-, 2,4-, 2,5- or 2,6-dimethylcyclohexyl, cycloheptyl or cyclooctyl;
- particularly suitable $C_7$-$C_{18}$-aralkyl, especially $C_7$-$C_{12}$-aralkyl, groups are alkyl-substituted phenylalkyl groups, eg. benzyl, 2-, 3- or 4-methylbenzyl, 2-phenylethyl, 3-phenylpropyl, 4-phenylbutyl, 2-, 3- or 4-ethylbenzyl, 3- or 4-isopropylbenzyl or 3- or 4-butylbenzyl;
- examples of suitable $C_6$-$C_{18}$-aryl groups are phenyl, 2-, 3- or 4-biphenylyl, α- or β-naphthyl, 2-, 3- or 4-methylphenyl, 2-, 3- or 4-ethylphenyl, 3- or 4-isopropylphenyl, 3- or 4-butyl-phenyl or 3- or 4-(2-ethylhexyl)phenyl; $C_6$-$C_{14}$-aryl groups are preferred, especially phenyl and alkyl-substituted phenyl;
- particularly suitable $C_3$-$C_{18}$-hetaryl groups are five- or six-membered $C_3$-$C_{12}$-hetaryl groups with one or two heteroatoms from the group of nitrogen, oxygen and sulfur; examples thereof are:

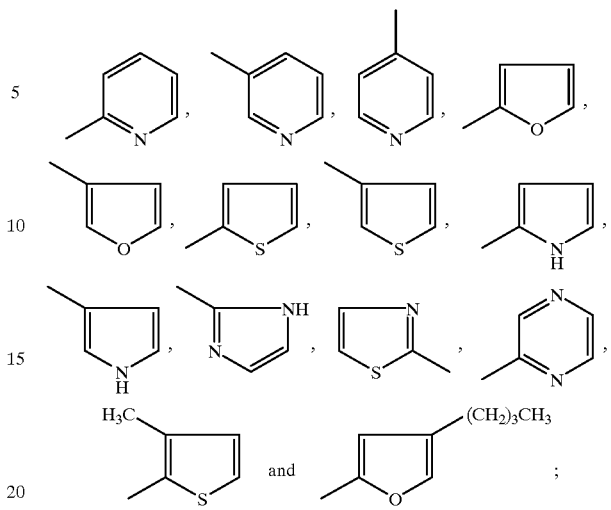

examples of suitable aliphatic radicals interrupted by oxygen or amino groups, especially NH or $N(CH_3)$ groups, are the following structures:

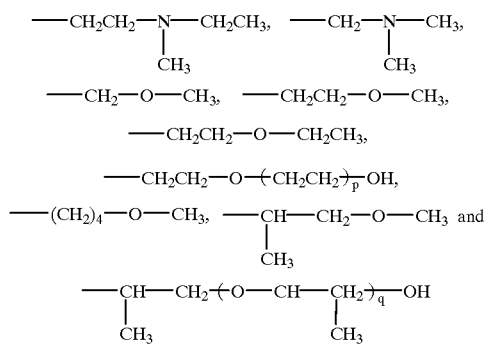

with p=2 to 8 and q=2 to 5.

The variable $Z^4$ in the cyclic oxime moieties $L^2$ can mean, in particular, $C_3$-$C_{12}$-alkylene groups of the following structure:

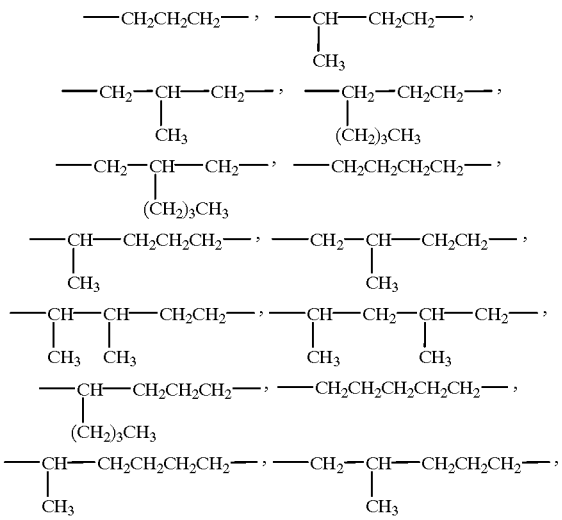

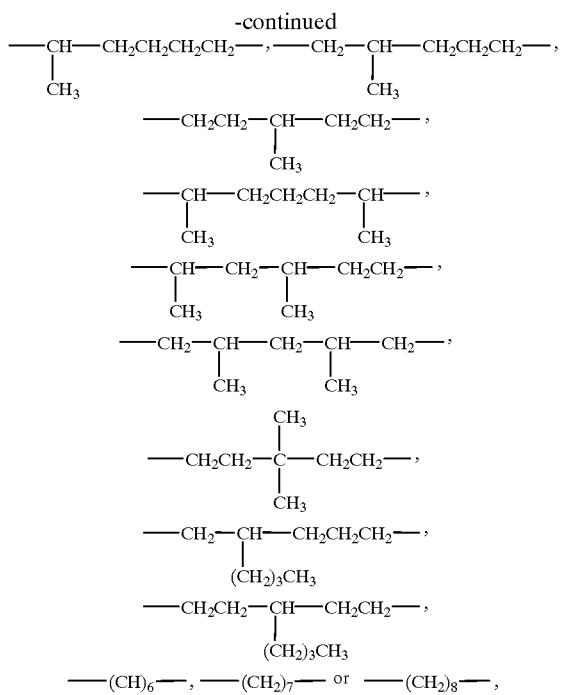

where the variable $Z^4$ can be functionalized or interrupted as stated.

The variables $Z^1$ to $Z^3$ in the heterocyclic systems (h), (j) and (k) can be, in particular, $C_2$-$C_{10}$-alkylene groups of the following structure:

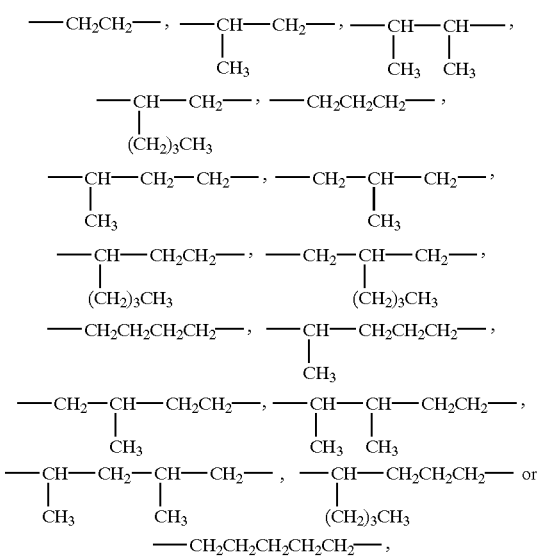

where, in the case of non-symmetrical alkylene groups, in principle both ways of incorporation into the rings are possible. The variables $Z^1$ to $Z^3$ can be functionalized or interrupted as stated.

Particularly suitable unsubstituted or substituted hydrocarbon radicals $R^1$ for the variable $L^3$ in the oxime esters II are $C_1$-$C_{18}$-alkyl radicals, $C_2$-$C_{18}$-alkenyl radicals, $C_7$-$C_{12}$-aralkyl radicals or phenyl or alkyl-substituted phenyl with a total of up to 14 carbon atoms. Typical examples thereof are: methyl, ethyl, n-propyl, n-butyl, n-pentyl, n-hexyl, n-heptyl, n-octyl, n-nonyl, n-decyl, n-dodecyl, n-tetradecyl, n-hexadecyl, n-octadecyl, benzyl, 2-phenylethyl, 4-phenylbutyl, phenyl and o-, m- or p-tolyl.

Particularly suitable carboxylic ester residues (a) for $L^3$ are:

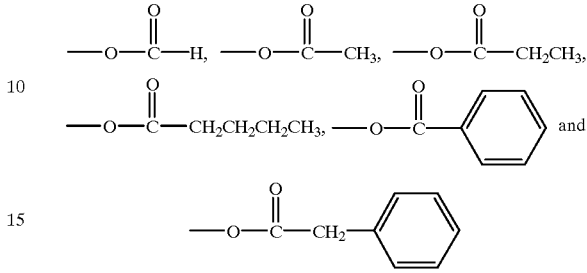

Particularly suitable carboxamide residues (b) for $L^3$ are:

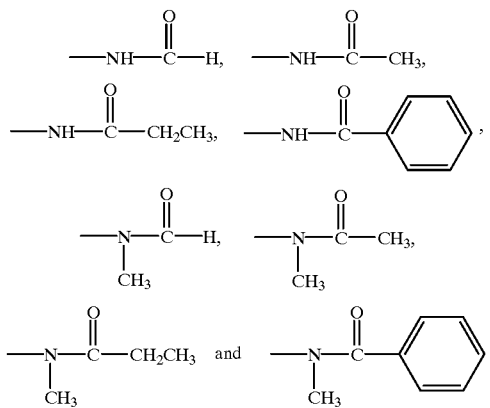

Particularly suitable phenolate residues (c) for $L^3$ are:

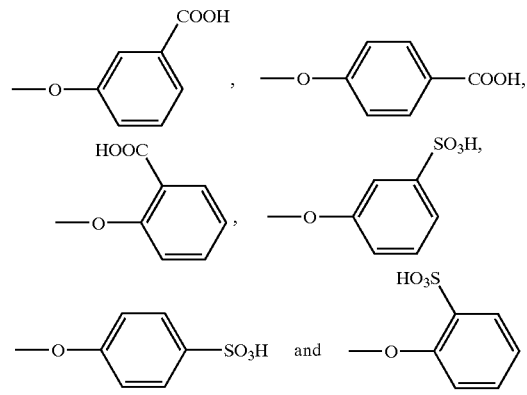

and the relevant sodium or potassium salts.

Particularly suitable vinyloxy radicals (d) for $L^3$ are:

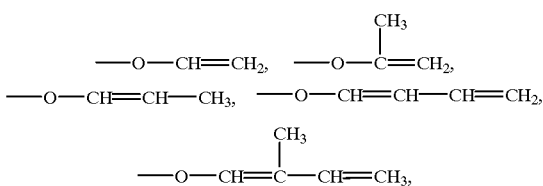

-continued

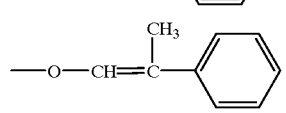

Particularly suitable sulfonamide residues (e) for $L^3$ are:

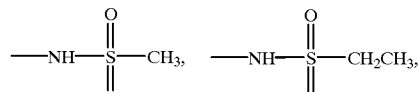

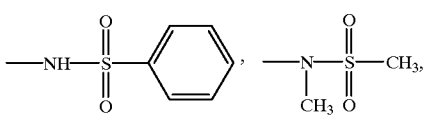

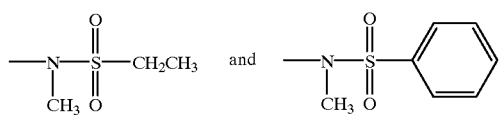

Particularly suitable imidazole residues (f) for $L^3$ are:

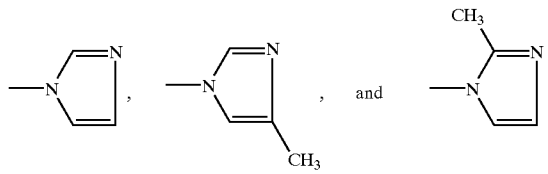

Particularly suitable amidolactam residues (g) for $L^3$ are:

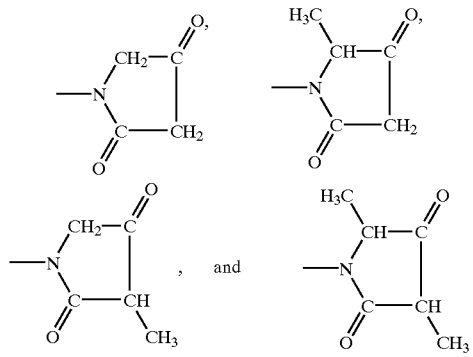

Particularly suitable cyclic carbamate residues (h) for $L^3$ are:

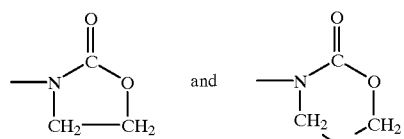

Particularly suitable lactonoxy residues (j) for $L^3$ are:

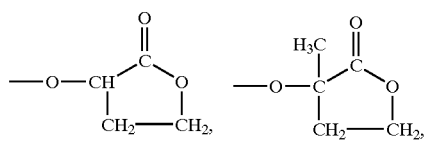

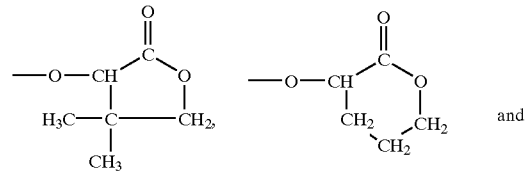

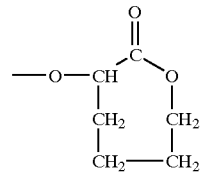

T in the general formula for the lactonoxy residue (j) is preferably hydrogen or methyl.

Particularly suitable lactam residues (k) for $L^3$ are:

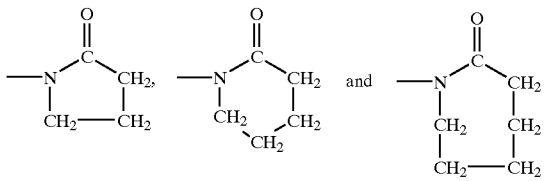

Typical examples of the linker A in the oxime esters II are like-wise those stated above for the oxygen-containing group X in the heterocyclic compounds I.

The linker A in the oxime esters II is, in particular, a chemical bond (formally derived from oxalic acid) or 1,2-ethylene (derived from succinic acid), 1,4-butylene (derived from adipic acid), hexamethylene (derived from suberic acid), octamethylene (derived from sebacic acid), 1,3- or 1,4-cyclohexylene or 1,2-, 1,3- or 1,4-phenylene (derived from phthalic acid, isophthalic acid or terephthalic acid).

The variables $R^1$, $R^2$, $R^3$, $Z^1$ to $Z^4$ and A defined above may additionally be functionalized by the stated groups. In this connection, $C_1$-$C_4$-alkoxy groups are, in particular, methoxy, ethoxy, n-propoxy, isopropoxy, n-butoxy, isobutoxy, sec-butoxy or tert-butoxy. Preferred amino groups are —NH$_2$, —NH(CH$_3$), —NH(CH$_2$CH$_3$), —N(CH$_3$)$_2$ and —N(CH$_2$CH$_3$)$_2$. Examples of carboxy-$C_1$-$C_4$-alkyl groups are carboxymethyl, carboxyethyl, carboxypropyl, carboxybutyl or carboxy-tert-butyl.

In a preferred embodiment there is use of oxime esters II in which $L^2$ is an oxime moiety of the formula

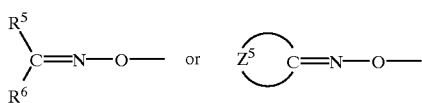

where $R^5$ and $R^6$ are hydrogen, $C_1$-$C_4$-alkyl, especially methyl or ethyl, phenyl or benzyl, and $Z^5$ is 1,4-butylene, 1,5-pentylene or 1,6-hexylene.

Aldoxime or ketoxime moieties of this type are derived from conventional aldehydes or ketones, for example from formaldehyde, acetaldehyde, propionaldehyde, benzaldehyde, phenylacetaldehyde, acetone, ethyl methyl ketone, diethyl ketone, acetophenone, henylacetone, benzophenone, cyclopentanone, cyclohexanone or cycloheptanone.

Furthermore, preferred oxime esters II are those where $L^3$ is a second oxime moiety $L^2$; particularly preferred in this connection are those oxime esters II where $L^2$ and $L^3$ are the same oxime moiety.

Of particular interest are bisoxime esters II derived from oxalic acid, succinic acid, adipic acid, phthalic acid, isophthalic acid or terephthalic acid and aliphatic ketones with 3 to 6 carbon atoms or from $C_5$-$C_7$-cycloalkanones. Systems of this type can be prepared in a simple manner, for example by reacting the corresponding dicarbonyl chlorides or bromides with appropriate aliphatic or cycloaliphatic ketoximes in the presence of bases.

Also of particular interest as bisoxime esters II are furthermore bisiminocarbonates which are formally derived from carbonic acid and aliphatic ketones with 3 to 6 carbon atoms or from $C_5$-$C_7$-cycloalkanones. Systems of this type can be prepared in a simple manner for example by reacting phosgene with the appropriate aliphatic or cycloaliphatic ketoximes in the presence of bases.

The oxime esters II described, methods for preparing them and their use as bleach activators in detergents, bleaches and cleaners are known in principle, for example from JP-A 06/336 468 (5), WO-A 93/04037 (6), the article by A. Jumar, P. Held and W. Schulze in Z. Chem. 7 (1967), 344–345 (7) or German Patent Application 1 95 41 012.2 (8). According to (7), non-symmetrical bisoxime esters II and monooxime esters II can be prepared in the case where m=0 (carbonic acid derivatives) via the intermediate stage of the corresponding chloroformyloxime.

It is, of course, also possible to employ mixtures of the hetero-cyclic compounds I with the oxime esters II in the solid compositions according to the invention.

A high internal surface area of the inert porous carrier materials is crucially important for the required properties of the resulting solid composition. The internal surface area is preferably in the range from 50 to 480 $m^2/g$, in particular 100 to 460 $m^2/g$, especially 180 to 450 $m^2/g$.

The average particle size of the inert porous carrier materials is also important but it can vary within a wider range than the internal surface area. The best results are obtained with an average particle size of from 10 nm to 100 $\mu$m, in particular 20 nm to 50 $\mu$m, especially 1 $\mu$m to 20 $\mu$m, but the average particle sizes can, depending on the nature of the carrier material and the application of the solid composition according to the invention, also be smaller, for example down to 3 nm, or larger, for example up to 2 mm, especially up to 500 $\mu$m.

Inert porous carrier materials which can be used are in principle all conventional types of such chemically inert materials. However, particularly suitable are silica gels, silicas, aluminum oxides, kaolins or aluminum silicates or mixtures thereof.

Silica gels are colloidal shaped or unshaped silicas with an elastic or a solid consistency and with a loose to compact pore structure and high adsorption capacity. Silica gel surfaces have acidic properties. Silica gel is usually prepared from water glass by reaction with mineral acids.

Silicas which can be employed are, besides the silicas prepared in a wet process, particularly advantageously the highly disperse pyrogenic $SiO_2$ types which are obtained thermally, ie. normally prepared by flash hydrolysis of $SiCl_4$ (eg. Aerosils® or Sipernats®). In a particularly preferred embodiment of the present invention, silica with an average (agglomerate) particle size of from 100 nm to 30 $\mu$m, in particular 1 $\mu$m to 20 $\mu$m, and an $SiO_2$ content of 95–100, preferably 98–100, % by weight is used.

Aluminum oxides occur in nature as, for example, aluminas or corundum. The aluminum oxide is in the a modification in these cases. Industrially, a-$Al_2O_3$ is obtained from bauxite by the Bayer process. "Active" aluminum oxides with a high specific surface area which are particularly suitable as adsorbents are prepared by precipitation processes from aluminum salt solutions or by calcination from α-aluminum hydroxide.

Kaolins are hydrated aluminum silicates (clays) which occur naturally in soil and which are also called china clays because of their former principal use. The main constituents are the triclinic kaolinite and the monoclinic dickite and nacrite together with montmorillonite and aluminum silicates in gel form (allophanes).

Aluminum silicates are compounds with various proportions of $Al_2O_3$ and $SiO_2$, which occur in nature as andalusite, disthene, mullite, sillimanite, etc. Aluminum silicate minerals in which Al occupies sites in the crystal lattice in place of Si are the alumosilicates (eg. ultramarines, zeolites, feldspars).

Freshly precipitated aluminum silicates are finely dispersed and have a large surface area and high adsorption capacity.

The ratio of heterocyclic compounds I or oxime esters II and inert porous carrier materials in the solid composition according to the invention can vary within certain limits depending on the method for preparing the solid composition and the material properties of the components employed. A preferred ratio is 10–95 parts by weight of I or II to 5–90 parts by weight of carrier, in particular 30–90 parts by weight of I or II to 10–70 parts by weight of carrier. The stated parts by weight of I or II are always based on anhydrous or solvent-free compound I or II. For economic reasons, it is desirable to maximize the proportion of heterocyclic compounds I or oxime esters II.

The solid composition according to the invention is, as a rule, homogeneously composed of the components employed. The hetero-cyclic compounds I and the oxime esters II and, where appropriate, other auxiliaries are uniformly drawn into the interior of the carrier material particles and are uniformly distributed therein, because they have a relatively large internal surface area. There is normally no noticeable gradient of concentration of the substances which are drawn in between the inner and outer surface of the particles or particle aggregates, so that it is not possible to speak of "coating".

It may be advantageous for the properties of the solid composition according to the invention if it contains, in addition to the stated parts by weight of I and II and carrier material, 0.5–70 parts by weight, in particular 2–40 parts by weight, especially 5–25 parts by weight, of anionic, nonionic or zwitterionic surfactants, carboxyl-containing polymers, polysaccharides, polyalkylene glycols, acidic alkali metal or alkaline earth metal salts of inorganic acids, neutral alkali metal salts, aliphatic $C_8$-$C_{18}$-monocarboxylic acids, aliphatic di-or tricarboxylic acids, aromatic mono- or dicarboxylic acids, it being possible for the abovementioned carboxylic acids additionally to contain hydroxyl and amino groups in the molecule, aliphatic $C_3$-$C_7$-monohydroxycarboxylic acids or mixtures thereof.

Examples of suitable anionic surfactants in this case are alkali metal salts of fatty acids (soaps), alkylbenzenesulfonates, alkanesulfonates, α-olefinsulfonates, hydroxyalkanesulfonate, α-sulfo fatty acid esters, alkyl sulfates, alkyl ether sulfates or fatty alcohol ether sulfates. Of these, alkylbenzene-sulfonates, especially the alkali metal and ammonium salts of linear $C_{11}$-$C_{13}$-alkylbenzenesulfonates, eg. sodium dodecylbenzenesulfonate, are preferred.

Examples of nonionic surfactants used in this case are alcohol alkoxylates, especially fatty alcohol alkoxylates, and alkylphenol alkoxylates, fatty acid alkylolamides and alkyl glycosides, especially $C_8$-$C_{16}$-monoalkyl glucosides. Of these, ethoxylates and propoxylates of saturated or unsaturated $C_{12}$-$C_{20}$ fatty alcohols, eg. coconut fatty and tallow fatty alcohol ethoxylates, are preferred.

Examples of suitable zwitterionic surfactants in this case are secondary and tertiary amine oxides.

Suitable carboxyl-containing polymers are, in particular, homopolymers of acrylic acid and methacrylic acid, and copolymers containing acrylic acid and/or methacrylic acid, and the relevant alkali metal or ammonium salts. Acrylic acid/maleic acid copolymers are particularly preferred, especially in partially neutralized form, eg. acrylic acid/maleic acid copolymer which is about 50% in the form of the sodium salt (acrylic acid:maleic acid ratio=70:30 by weight).

The most advantageous polysaccharides are starch, amylose and derivatives of these naturally occurring polysaccharides such as carboxymethylcellulose, cellulose acetate hydrogen phthalate, ethylcellulose or sulfated cellulose ethers. Of these, it is possible to employ starch itself most favorably.

Particularly suitable polyalkylene glycols are polyethylene glycols and ethylene oxide/propylene oxide copolymers.

Particularly suitable acidic alkali metal and alkaline earth metal salts of inorganic acids are sodium bicarbonate and sodium bisulfate, but also potassium bicarbonate, potassium bisulfate, sodium dihydrogen phosphate, potassium dihydrogen phosphate, disodium hydrogen phosphate, dipotassium hydrogen phosphate, calcium hydrogen phosphate or magnesium hydrogen phosphate.

Particularly suitable neutral alkali metal salts are sodium sulfate and sodium chloride.

Examples of suitable aliphatic $C_8$-$C_{18}$-monocarboxylic acids, aliphatic di- or tricarboxylic acids, aromatic mono- or dicarboxylic acids, it being possible for the abovementioned carboxylic acids additionally to contain hydroxyl and amino groups in the molecule, and aliphatic $C_3$-$C_7$-monohydroxy carboxylic acids are fatty acids such as lauric acid, myristic acid, palmitic acid and stearic acid, oxalic acid, malonic acid, succinic acid, glutaric acid, adipic acid, pimelic acid, suberic acid, maleic acid, fumaric acid, tartaric acid, malic acid, citric acid, benzoic acid, salicylic acid, anthranilic acid, sulfanilic acid, phthalic acid, α- and β-naphthoic acid, naphthalic acid and lactic acid. Of these, palmitic acid, stearic acid, oxalic acid, malonic acid, succinic acid, glutaric acid, adipic acid, pimelic acid, tartaric acid, citric acid and benzoic acid are preferred. Said carboxylic acids mainly improve the color stability on storage in detergent powders.

It is also possible to employ mixtures of several of said additives from one of the listed groups or from different groups.

The invention also relates to a process for preparing the described solid composition, which comprises mixing together 5–98 parts by weight of heterocyclic compounds I and/or oxime esters II with 2–95 parts by weight of inert porous carrier materials in a conventional way and converting this mixture where appropriate by conventional methods into a formulated form suitable for the particular application.

In a preferred embodiment, this preparation process is carried out in such a way that a solution or a melt of the heterocyclic compounds I and/or of the oxime esters II is mixed with the inert porous carrier materials by stirring in, spraying on or impregnating, the solvent, where present, is substantially removed by distillation or drying and, if necessary, the resulting mixture is converted, where appropriate after mixing with other auxiliaries, by conventional methods into a formulated form suitable for the particular application. Solvents suitable for this purpose are, in particular, conventional organic solvents such as alcohols, eg. methanol, ethanol or isopropanol, ketones, eg. acetone, carboxylic esters, eg. methyl or ethyl acetate, or unhalogenated or halogenated hydrocarbons, eg. n-hexane, cyclohexane, toluene, xylene or chlorobenzene.

A typical preparation process of this type entails the inert porous carrier materials being introduced into the solution of the compounds I or II in an organic solvent and, where appropriate, admixing other auxiliaries, in particular surfactants. The solvent is subsequently removed virtually completely, which is advantageously carried out by distillation at low temperature under reduced pressure, especially when a relatively high-boiling solvent has been employed. Then, if necessary, the product, which results in the form of a free-flowing powder, is subjected to conventional methods of compaction, where appropriate size reduction and screening to a size fraction in the range from, for example, 200 μm to 3 mm -depending on the application.

If necessary, the storage stability of the solid composition according to the invention can be improved by other subsequent treatments, for example by coating with fats, oils, melts or solutions.

In place of the introduction and admixing (stirring in) of the carrier materials, the solution of the compounds I or II can also be sprayed onto the carrier materials by conventional techniques. Impregnation processes can also be used. If the mixtures after the spraying or impregnation process are already in powder form, they can also be agglomerated directly without further drying in a conventional mixer, it being necessary where appropriate to add other auxiliaries, especially surfactants, for example in molten form or as highly concentrated aqueous solution, and this is followed, where appropriate, by the processing to the required size fraction described above.

The solid composition according to the invention is mainly suitable as a solid additive for detergents, bleaches and cleaners, in particular as stable bleach activator component in such compositions.

It is thus possible to formulate detergents, bleaches and cleaners which contain 0.1–30% by weight, based on the total amount of the formulation, of the solid composition according to the invention. The present invention likewise relates to these detergents, bleaches and cleaners. Other conventional components in detergents, bleaches and cleaners are explained in detail below:

The cold bleach activators I and II described form the bleach system together with bleaches, as a rule peroxy compounds, which are likewise present in the formulation, normally separately. It is moreover possible for the pH of the washing or bleaching or cleaning liquors to vary within wide limits, from the weakly acidic region (pH 4) to the highly alkaline region (pH 13) depending on the application. The alkaline range from pH 8 to pH 11 is preferred because it is particularly advantageous for the activation reaction and the stability of the peroxy compound formed.

For this reason, the bleach activators described are also preferably used together with a sodium perborate or a sodium carbonate perhydrate, the solutions of which already have pH values in this range. Examples of other suitable peroxy compounds are phosphate perhydrates and urea perhydrate. It may also occasionally be expedient to change the pH of the medium again, especially into the acidic region, by suitable additives after the activation reaction has taken place.

The amounts of bleaches (peroxy compounds) employed are generally chosen so that the liquors contain from 10 to 10,000 ppm active oxygen, preferably from 50 to 5,000 ppm active oxygen. The amount of bleach activator used also depends on the application. From 0.03 to 1.0 mol, preferably 0.1 to 0.5 mol, of activator is used per mole of inorganic peroxy compound, depending on the required degree of activation, but amounts above or below these limits are also possible in special cases.

Particularly suitable additional bleach activators which can be employed in combination with the heterocyclic compounds I or the oxime esters II (in the solid composition according to the invention or as possibly formulated separate component) are:

polyacylated sugars, eg. pentaacetylglucose;

acyloxybenzenesulfonic acids and their alkali metal and alkaline earth metal salts, eg. sodium p-isononanoyloxybenzene-sulfonate or sodium p-benzoyloxybenzenesulfonate;

N,N-diacylated and N,N,N',N'-tetraacylated amines, eg. N,N,N',N'-tetraacetylmethylenediamine and -ethylenediamine, N,N-diacetylaniline, N,N-diacetyl-p-toluidine or 1,3-diacylated hydantoins such as 1,3-diacetyl-5,5-dimethylhydantoin;

N-alkyl-N-sulfonylcarbonamides, eg. N-methyl-N-mesylacetamide or N-methyl-N-mesylbenzamide;

N-acylated cyclic hydrazides, acylated triazoles or urazoles, eg. monoacetylated maleic hydrazide;

O,N,N-trisubstituted hydroxylamines, eg. O-benzoyl-N,N-succinylhydroxylamine, O-acetyl-N,N-succinylhydroxylamine or O,N,N-triacetylhydroxylamine;

N,N'-diacylsulfamides, eg. N,N'-dimethyl-N,N'-diacetylsulfamide or N,N'-diethyl-N,N'-dipropionylsulfamide;

triacylcyanurates, eg. triacetylcyanurate or tribenzoylcyanurate;

carboxylic anhydrides, eg. benzoic anhydride, m-chlorobenzoic anhydride or phthalic anhydride;

1,3-diacyl-4,5-diacyloxyimidazolines, eg. 1,3-diacetyl-4,5-diacetoxyimidazoline;

tetraacetylglycoluril and tetrapropionylglycoluril;

diacylated 2,5-diketopiperazines, eg. 1,4-diacetyl-2,5-diketopiperazine;

acylation products of propylenediurea and 2,2-dimethylpropylenediurea, eg. tetraacetylpropylenediurea;

α-acyloxypolyacylmalonamides, eg. α-acetoxy-N,N'-diacetylmalonamide;

diacyldioxohexahydro-1,3,5-triazines, eg. 1,5-diacetyl-2,4-dioxohexahydro-1,3,5-triazine;

benzo-(4H)1,3-oxazin-4-one with alkyl radicals, eg. methyl, or aromatic radicals, eg. phenyl, in position 2.

For textile laundering, the bleach activators described can be combined with virtually all conventional ingredients of detergent formulations. It is possible in this way to design formulations suitable specifically for textile treatment at low temperatures, and those suitable in several temperature ranges up to the traditional boiling wash range.

The principal ingredients of such detergent formulations are, besides bleaches (peroxy compounds) and bleach activators, builders and surfactants. These compositions may also contain other conventional auxiliaries and additives such as antiredeposition agents, peroxide stabilizers, electrolytes, optical brighteners, enzymes, perfume oils, foam regulators and activating substances if expedient. The components of bleach and cleaner formulations are in principle the same.

Examples of conventional builders are condensed phosphates, alkali metal silicates, alkali metal carbonates, salts of amino carboxylic acids such as nitrilotriacetic acid, salts of polyphosphonic acids such as hydroxyethanediphosphonic acid, salts of polycarboxylic acids such as citric acid or polyacrylic acid and insoluble sodium aluminum silicates of the zeolite NaA and NaX types.

Particularly suitable surfactants are those of the nonionic and synthetic anionic surfactant types. Examples of nonionic surfactants are the polyethylene glycol monoalkyl and monophenyl ethers prepared from long-chain alcohols or alkylphenols and ethylene oxide, and the long-chain alkyl glycosides.

The anionic surfactants are primarily sulfates and sulfonates of long-chain compounds, for example alkylbenzenesulfonates, fatty acid ester sulfonates, alkanesulfonates, olefin sulfonates, fatty alcohol sulfates and sulfates of polyethylene glycol monoethers. It is furthermore possible to use soaps and salts of long-chain acylcyanamides, and long-chain succinates and sulfosuccinates.

Typical textile detergents and bleaches of these types have approximately the following composition:

0.5–30% by weight, preferably 5–25% by weight, of anionic and/or nonionic surfactants, 0.5–60% by weight, preferably 5–50% by weight, of builders from the group of condensed phosphates, alkali metal silicates, alkali metal carbonates, sodium aluminum silicates and mixtures thereof, 0–20% by weight, preferably 0.5–8% by weight, of builders from the group of salts of amino carboxylic acids, salts of polyphosphonic acids, salts of polycarboxylic acids and mixtures thereof, 2–35% by weight, preferably 5–30% by weight, of inorganic peroxy compounds, 0.1–30% by weight, preferably 0.5–20% by weight, of the solid composition according to the invention, ad 100% conventional auxiliaries and additives and water.

The solid composition according to the invention has the advantage that it has a sufficiently long shelf life, ie. remains free-flowing without forming lumps or agglomerates. During this storage time there are negligible losses of activity, for example in respect of the bleaching action. Detergents, bleaches and cleaners which contain the solid composition according to the invention are usually more effective than those containing conventional bleach activators such as N,N,N',N'-tetraacetyl-ethylenediamine (TAED) in the same amounts.

PREPARATION EXAMPLES

Example 1

10 g of N-(n-octanoyl)-ε-caprolactam were dissolved in 20 g of acetone, and 10 g of highly disperse silica with an internal surface area of about 190 $m^2/g$ and an average particle size of about 7 μm (Sipernat®22S from Degussa) were added. After thorough mixing of the suspension, the solvent was removed by distillation to leave a dry, free-flowing powder which contained the cold bleach activator uniformly dispersed.

Example 2

10 g of N-(n-octanoyl)-ε-caprolactam were dissolved in 20 g of acetone, and 10 g of the same highly disperse silica as in Example 1, 2 g of sodium sulfate, 2 g of citric acid and 1 g of corn starch were added. After thorough mixing of the suspension, the solvent was removed by distillation to leave a dry, free-flowing powder which contained the cold bleach activator uniformly dispersed.

Technical Investigations of Use

Washing tests were carried out with hydrophilic and hydrophobic test soilings using the product from Example 2, and, for comparison, using unformulated N-(n-octanoyl)-ε-caprolactam and N,N,N',N'-tetraacetylethylenediamine (TAED). It emerged from this that the bleach activator formulated according to the invention has a distinctly greater bleaching action, especially with hydrophobic soilings such as grass on cotton, than the bleach activator TAED which represents the prior art (see Table 1). The test was carried out in a launder-o-meter, Atlas standard type, using a heavy duty detergent of the following composition (% by weight):

| | |
|---|---|
| linear alkylbenzenesulfonate (50% by weight) | 0.8 |
| conventional soap | 0.4 |
| conventional fatty alcohol sulfate | 12.0 |
| $C_{13}/C_{15}$-Oxo alcohol reacted with 7 mol of ethylene oxide | 4.7 |
| Magnesium silicate | 0.8 |
| Sodium bicarbonate | 9.0 |
| Sodium percarbonate | 18.0 |
| Sodium sulfate | 3.2 |
| Sodium citrate dihydrate | 5.0 |
| Conventional sheet silicate | 14.0 |
| Zeolite A | 15.0 |
| Carboxymethylcellulose | 0.6 |
| Water | Remainder to 100 |

The concentration of bleach activator employed in Table 1 or 2 was in each case 5% by weight of active substance based on the amount of detergent.

The tests were carried out under the following conditions:

| | |
|---|---|
| Amount of liquor: | 250 g |
| Water hardness: | 3.0 mmol/l |
| Ca/Mg/HCO$_3$ molar ratio: | 4:1:8 |
| Detergent dose: | 4.5 g/l |
| Temperature: | 22° C./38° C./60° C. |
| Washing time: | 30 min |
| Soiled fabric 1: | 2.5 g of bleached cotton (WFK Krefeld) soiled with chlorophyll |
| Soiled fabric 2: | 2.5 g of bleached cotton soiled with red wine |
| Soiled fabric 3: | 2.5 g of unbleached cotton cheesecloth |
| Rinsing: | 3 × 30 sec with tapwater (14° German hardness) |

The tests were evaluated by measurements of the reflectance on the dried fabrics. The color strength of each of the test soilings before and after the washing were determined by the method described by A. Kud, Seifen, öle, Fette, Wachse 119 (1993) 590–594 from the measurements of the reflectance at 18 wavelengths in the range from 400 to 700 nm at intervals of 20 nm on the individual test fabrics, and the absolute bleaching action $A_{abs}$ in % was calculated therefrom. The bleaching action in % is indicated in the following tables.

TABLE 1

Test fabric soiled with grass

| Bleach activator | Temperature 22° C. | 38° C. | 60° C. |
|---|---|---|---|
| TAED | 27.2 | 32.0 | 41.7 |
| Example 2 (formulated) | 30.8 | 37.6 | 46.2 |

TABLE 2

| Bleach activator | Temperature 22° C. | 38° C. | 60° C. |
|---|---|---|---|
| a) Soiling with chlorophyll | | | |
| Octanoylcaprolactam | 31.1 | 39.5 | 45.6 |
| Example 2 (formulated) | 30.8 | 37.6 | 46.2 |
| b) Soiling with red wine | | | |
| Octanoylcaprolactam | 60.3 | 64.0 | 70.6 |
| Example 2 (formulated) | 63.8 | 67.6 | 73.9 |
| c) Unbleached cotton cheesecloth | | | |
| Octanoylcaprolactam | 7.1 | 14.1 | 14.2 |
| Example 2 (formulated) | 9.1 | 13.9 | 19.6 |

The results of measurements from the washing tests in Table 2 show that the formulation, represented by the example of octanoylcaprolactam, does not necessarily entail a loss of effect.

We claim:

1. A solid composition consisting essentially of 5–98 parts by weight of heterocyclic compounds of the general formula I $$R^1\text{—}X\text{—}L^1 \qquad (I)$$

where $L^1$ is (a) a cyclic carbamate residue of the formula

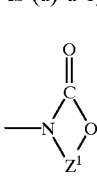

(c) a lactam residue of the formula

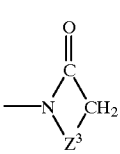

where $Z^1$ and $Z^3$ are 1,2-, 1,3-, 1,4- or 1,5-alkylene groups which have 4 to 20 carbon atoms, and which can additionally be functionalized by one to three hydroxyl groups, $C_1$-$C_4$-alkoxy groups, amino groups, $C_1$-$C_4$- alkylamino groups, di-$C_1$-$C_4$-alkylamino groups, chlorine atoms, bromine atoms, nitro groups, cyano groups, carboxyl groups, sulfo groups, carboxy-$C_1$-$C_4$-alkyl groups, carboxamide groups or phenyl, tolyl or benzyl radicals, it likewise being possible for aromatic nuclei in turn to be substituted by said radicals, or interrupted by one or two non-adjacent oxygen atoms, amino groups, $C_1$-$C_4$-alkylamino groups or carbonyl groups, and X is an oxygen-containing group of the formula

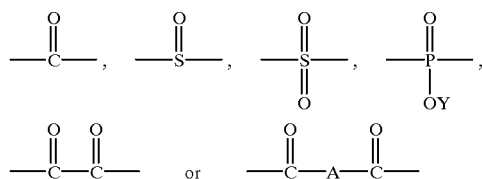

where

Y is hydrogen, ammonium which can be unsubstituted or substituted by organic radicals, or $C_1$-$C_4$-alkyl, and A is a chemical bond or a $C_1$-$C_{18}$-alkylene group, a $C_2$-$C_{18}$-alkenylene group, a $C_5$-$C_{32}$-cycloalkylene group, a $C_7$-$C_{30}$-aralkylene group, a $C_6$-$C_{18}$-arylene group or a $C_3$-$C_{18}$-hetarylene group, it additionally being possible for aliphatic structural units to be functionalized by one to five hydroxyl groups, $C_1$-$C_4$-alkoxy groups, amino groups, $C_1$-$C_4$-alkylamino groups, di-$C_1$-$C_4$-alkylamino groups, chlorine atoms, bromine atoms, nitro groups, cyano groups, carboxyl groups, sulfo groups, carboxy-$C_1$-$C_4$-alkyl groups, carboxamide groups or phenyl, tolyl or benzyl radicals, it likewise being possible for aromatic, cycloaliphatic and heteroaromatic structural units to be substituted by said radicals, or interrupted by one to eight non-adjacent oxygen atoms, amino groups, $C_1$-$C_4$-alkylamino groups or carbonyl groups, and $R^1$ has the following meaning:

$C_1$-$C_{30}$-alkyl, $C_2$-$C_{30}$-alkenyl, $C_5$-$C_{18}$-cycloalkyl, $C_7$-$C_{18}$-aralkyl, $C_6$-$C_{18}$-aryl or $C_3$-$C_{18}$-hetaryl, it being additionally possible for aliphatic radicals to be functionalized by one to five hydroxyl groups, $C_1$-$C_4$-alkoxy groups, amino groups, $C_1$-$C_4$-alkylamino groups, di-$C_1$-$C_4$-alkylamino groups, chlorine atoms, bromine atoms, nitro groups, cyano groups, carboxyl groups, sulfo groups, carboxy-$C_1$-$C_4$-alkyl groups, carboxamide groups or phenyl, tolyl or benzyl radicals, it likewise being possible for aromatic, cyclo-aliphatic and heteroaromatic structural units to be substituted by said radicals, or interrupted by one to eight non-adjacent oxygen atoms, amino groups, $C_1$-$C_4$-alkylamino groups or carbonyl groups, or a heterocyclic radical $L^1$, and 2–95 parts by weight of inert porous carrier materials with an internal surface area of from 50 to 480 $m^2/g$.

2. A solid composition as claimed in claim 1, wherein the inert porous carrier materials have an average particle size of from 3 nm to 2 mm.

3. A solid composition as claimed in claim 1, wherein silica gels, silicas, aluminum oxide, kaolins and/or aluminum silicates are employed as inert porous carrier materials.

4. A solid composition as claimed in claim 1, wherein the oxygen-containing group X in the heterocyclic compounds I is

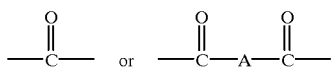

5. A solid composition as claimed in claim 1, wherein the radical $R^1$ in the heterocyclic compounds I is $C_6$-$C_{18}$-alkyl, $C6$-$C_{18}$-alkenyl, $C_7$-$C_{12}$-aralkyl, phenyl or alkylsubstituted phenyl with a total of up to 14 carbon atoms or a second heterocyclic radical $L^1$ which has the same structure as the first heterocyclic radical $L^1$.

6. A composition according to claim 1, wherein $L^1$ is a lactam residue and X is carbonyl.

7. A composition according to claim 1 wherein the heterocyclic compound of the general formula (I) is octanoyl-caprolactam.

8. The solid composition as claimed in claim 1, wherein the inert porous carrier materials have an internal surface area of 100 to 460 $m^2/g$.

9. The solid compositions as claimed in claim 1, wherein the inert porous carrier materials have an internal surface of 180 to 450 $m^2/g$.

10. The solid composition as claimed in claim 1, wherein the inert porous carrier is selected from the group consisting of silica gels, silicas, aluminum oxide, and kaolins.

11. The solid composition as claimed in claim 1, wherein $L^1$ is (a) a cyclic carbamate residue of the formula:

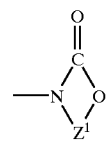

wherein $Z^1$ is a 1,2-, 1,3-, 1,4- or 1,5-alkylene group which has 4 to 20 carbon atoms, and which can additionally be functionalized by one to three hydroxyl groups, $C_1$-$C_4$-alkoxy groups, amino groups, $C_1$-$C_4$-alkylamino groups, di-$C_1$-$C_4$-alkylamino groups, chlorine atoms, bromine atoms, nitro groups, cyano groups, carboxyl groups, sulfo groups, carboxy-$C_1$-$C_4$-alkyl groups, carboxamide groups or phenyl, tolyl or benzyl radicals, it likewise being possible for aromatic nuclei in turn to be substituted by said radicals, or interrupted by one or two non-adjacent oxygen atoms, amino groups, $C_1$-$C_4$-alkylamino groups or carbonyl groups.

12. The solid composition as claimed in claim 1, wherein $L^1$ is (a) a lactam residue of the formula:

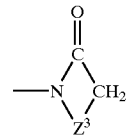

wherein $Z^3$ is a 1,2-, 1,3-, 1,4- or 1,5-alkylene group which has 4 to 20 carbon atoms, and which can additionally be functionalized by one to three hydroxyl groups, $C_1$-$C_4$-alkoxy groups, amino groups, $C_1$-$C_4$-alkylamino groups, di-$C_1$-$C_4$-alkylamino groups, chlorine atoms, bromine atoms, nitro groups, cyano groups, carboxyl groups, sulfo groups, carboxy-$C_1$-$C_4$-alkyl groups, carboxamide groups or phenyl, tolyl or benzyl radicals, it likewise being possible for aromatic nuclei in turn to be substituted by said radicals, or interrupted by one or two non-adjacent oxygen atoms, amino groups, $C_1$-$C_4$-alkylamino groups or carbonyl groups.

13. The solid composition as claimed in claim 1, wherein $R^1$ has the following meaning:

$C_1$-$C_{30}$-alkyl, $C_2$-$C_{30}$-alkenyl, $C_5$-$C_{18}$-cycloalkyl, $C_7$-$C_{18}$-aralkyl, $C_6$-$C_{18}$-aryl or $C_3$-$C_{18}$-hetaryl, it being additionally possible for aliphatic radicals to be functionalized by one to five hydroxyl groups, $C_1$-$C_4$-alkoxy groups, amino groups, $C_1$-$C_4$-alkylamino groups, di-$C_1$-$C_4$-alkylamino groups, chlorine atoms, bromine atoms, nitro groups, cyano groups, carboxyl groups, sulfo groups, carboxy-$C_1$-$C_4$-alkyl groups, carboxamide groups or phenyl, tolyl or benzyl radicals, it likewise being possible for aromatic, cyclo-aliphatic and heteroaromatic structural units to be substituted by said radicals, or interrupted by one to eight non-adjacent oxygen atoms, amino groups, $C_1$-$C_4$-alkylamino groups or carbonyl groups.

14. The solid composition as claimed in claim 1, wherein $R^1$ is $L^1$, and wherein $L^1$ is:

(a) a cyclic carbamate residue of the formula

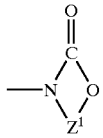

or (c) a lactam residue of the formula

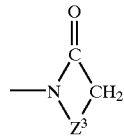

where $Z^1$ and $Z^3$ are 1,2-, 1,3-, 1,4- or 1,5-alkylene groups which have 4 to 20 carbon atoms, and which can additionally be functionalized by one to three hydroxyl groups, $C_1$-$C_4$-alkoxy groups, amino groups, $C_1$-$C_4$-alkylamino groups, di-$C_1$-$C_4$-alkylamino groups, chlorine atoms, bromine atoms, nitro groups, cyano groups, carboxyl groups, sulfo groups, carboxy-$C_1$-$C_4$-alkyl groups, carboxamide groups or phenyl, tolyl or benzyl radicals, it likewise being possible for aromatic nuclei in turn to be substituted by said radicals, or interrupted by one or two non-adjacent oxygen atoms, amino groups, $C_1$-$C_4$-alkylamino groups or carbonyl groups.

15. A process for preparing a solid composition as claimed in claim 1, which comprises mixing together 5–98 parts by weight of at least one heterocyclic compounds having the formula I with 2–95 parts by weight of inert porous carrier material.

16. A process for preparing a solid composition as claimed in claim 15, wherein a solution or a melt of the heterocyclic compound having the formula I is mixed with the inert porous carrier material by stirring in, spraying on or impregnating, and, optionally substantially removing the solvent, where present, by distillation or drying.

17. A detergent, bleach or cleaner comprising 0.1–30% by weight, based on the total amount of the formulation, of the solid composition as claimed in claim 1.

* * * * *

UNITED STATES PATENT AND TRADEMARK OFFICE
CERTIFICATE OF CORRECTION

PATENT NO. : 6,451,753 B2  Page 1 of 1
DATED : September 17, 2002
INVENTOR(S) : Oetter et al.

It is certified that error appears in the above-identified patent and that said Letters Patent is hereby corrected as shown below:

<u>Title page,</u>
Item [45] and the Notice information should read as follows:

-- [45] **Date of Patent: \*Sep. 17, 2002**

[\*] Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days. --

Signed and Sealed this

Fifteenth Day of April, 2003

JAMES E. ROGAN
*Director of the United States Patent and Trademark Office*